United States Patent [19]

Margulies

[11] 4,445,895

[45] May 1, 1984

[54] PREPACKAGED, DISPOSABLE HYPODERMIC SYRINGES

[75] Inventor: Herman Margulies, South Orange, N.J.

[73] Assignee: Sterling Drug Inc., New York, N.Y.

[21] Appl. No.: 434,844

[22] Filed: Oct. 18, 1982

Related U.S. Application Data

[62] Division of Ser. No. 284,054, Jul. 16, 1981.

[51] Int. Cl.$^3$ ............................................. A61M 5/00
[52] U.S. Cl. ..................................... 604/193; 604/201
[58] Field of Search ................ 604/193, 192, 200, 201

[56] References Cited

U.S. PATENT DOCUMENTS

| | | | |
|---|---|---|---|
| 2,524,367 | 10/1950 | Smith | 128/218 D |
| 2,865,372 | 12/1958 | Miskel et al. | 128/218 D |
| 2,904,043 | 9/1959 | Friedman | 128/218 D |
| 3,150,661 | 9/1964 | Maki . | |
| 3,375,825 | 4/1968 | Keller . | |
| 3,908,654 | 9/1975 | Lhoest et al. | 128/218 D X |

FOREIGN PATENT DOCUMENTS

| | | | |
|---|---|---|---|
| 1073156 | 1/1960 | Fed. Rep. of Germany ... | 128/218 D |
| 2450376 | 4/1976 | Fed. Rep. of Germany ...... | 128/218 DA |

*Primary Examiner*—John D. Yasko
*Attorney, Agent, or Firm*—William G. Webb; B. Woodrow Wyatt

[57] ABSTRACT

Prepackaged, disposable hypodermic syringes having a double-ended hypodermic needle comprising a cartridge ampoule and a syringe holder, as well as the syringe holders per se, are provided with restraint means to prevent accidental engagement between the hypodermic needle and the cartridge ampoule and consequent premature discharge of the ampoule contents prior to intended use.

30 Claims, 12 Drawing Figures

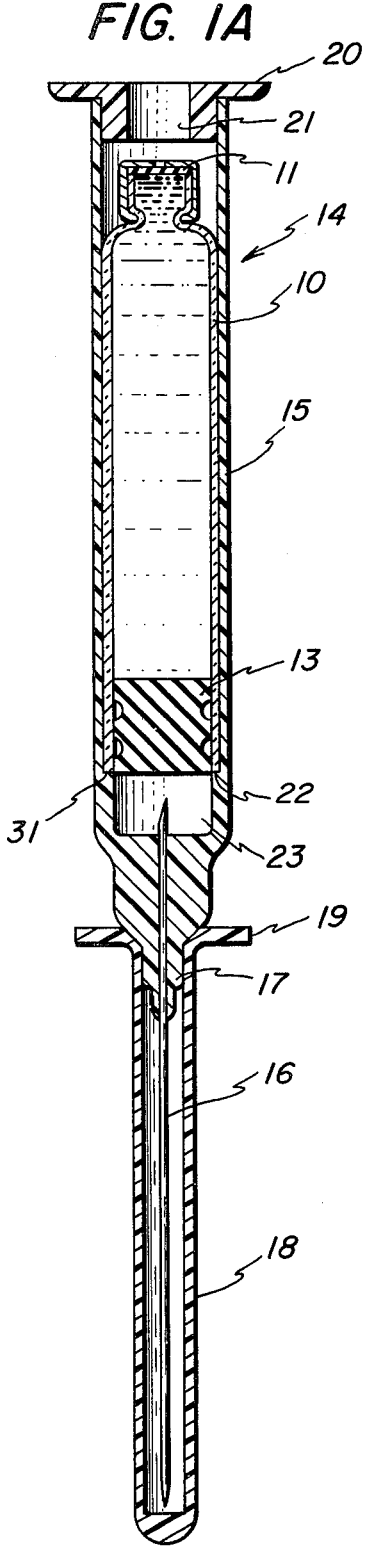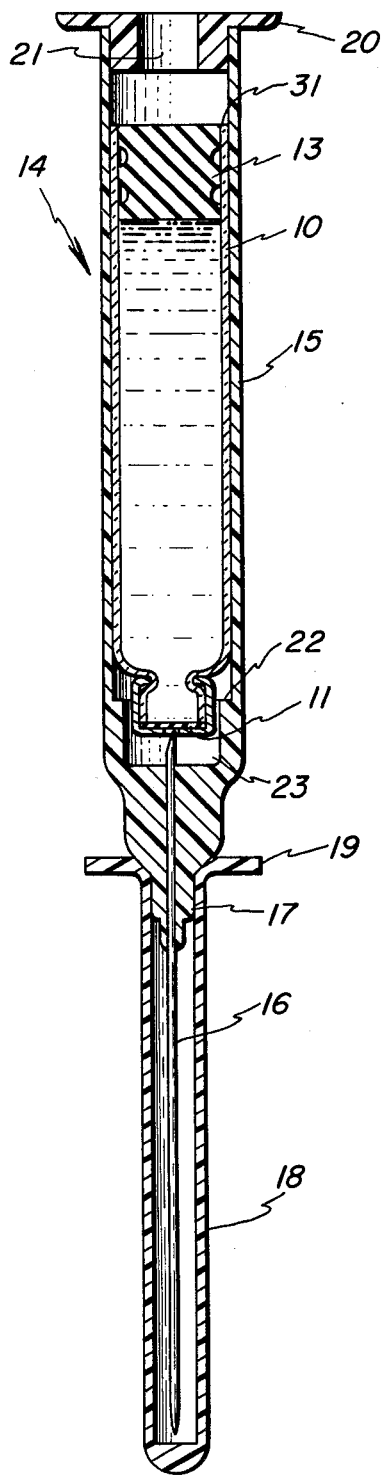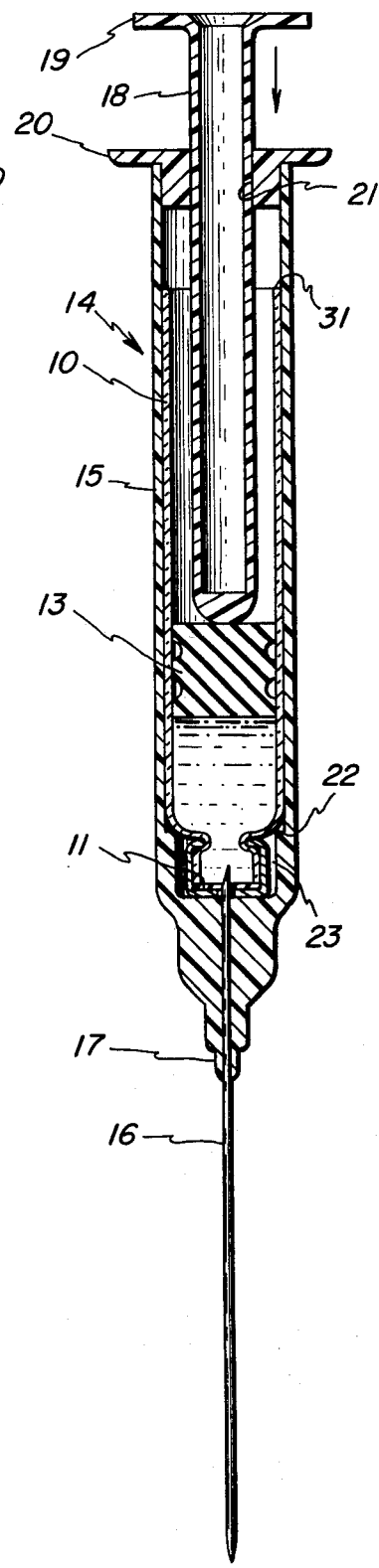

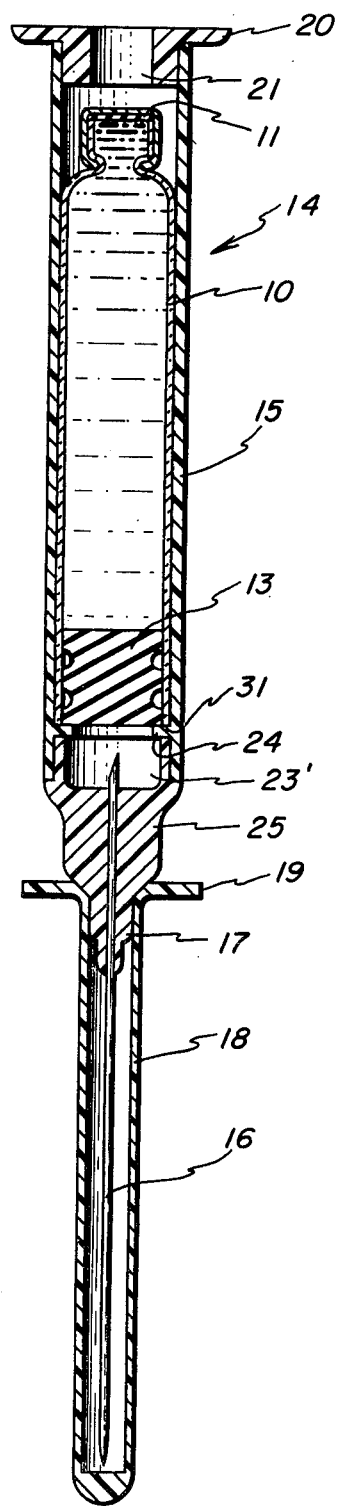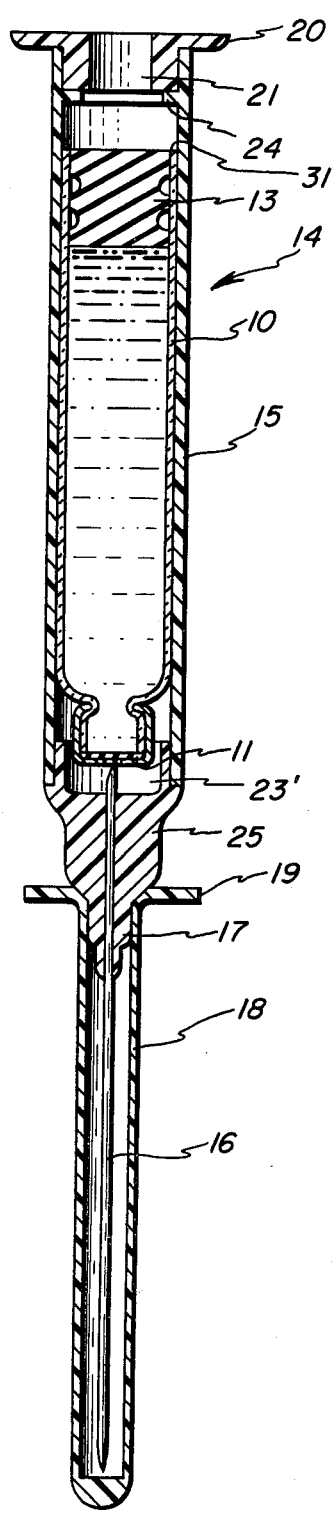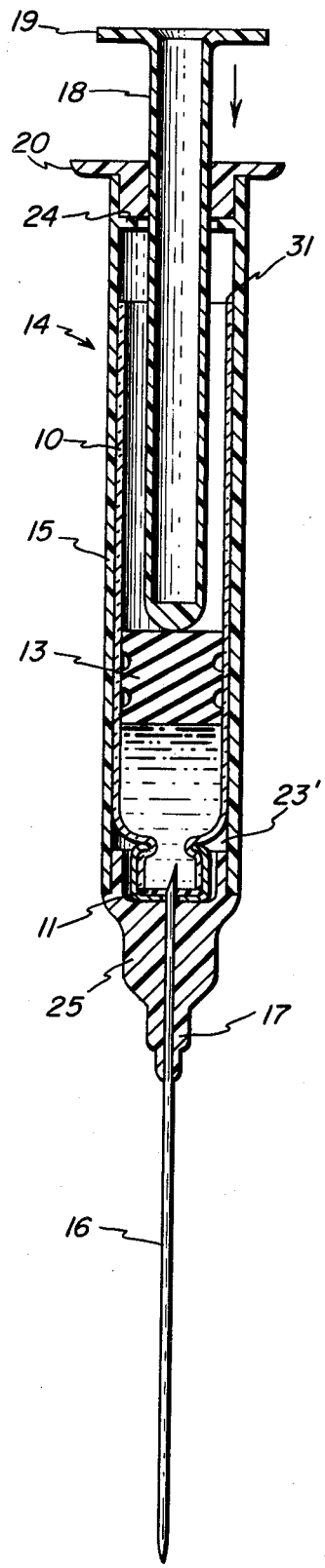

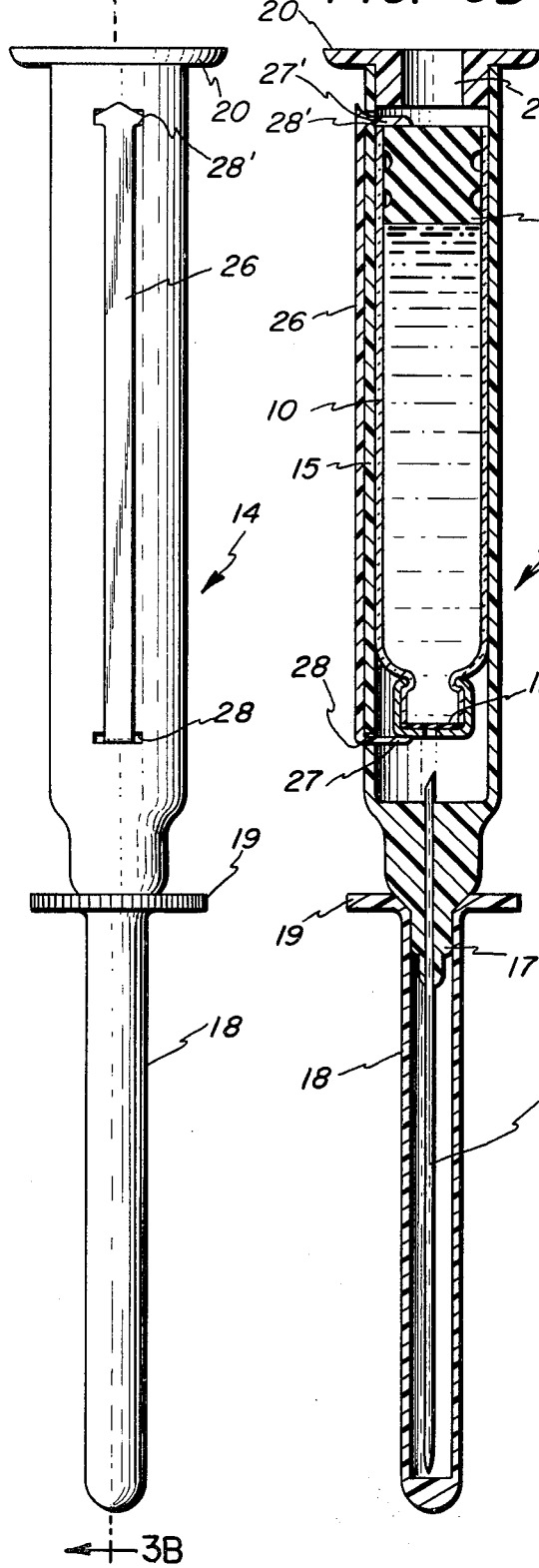

PREPACKAGED, DISPOSABLE HYPODERMIC SYRINGES

RELATED APPLICATIONS

This is a division of my prior, copending application Ser. No. 284,054, filed July 16, 1981.

BACKGROUND OF THE INVENTION (a) Field of the Invention

This invention relates to prepackaged, disposable hypodermic syringes having a double-ended hypodermic needle, for use in combination with medicament containing cartridge ampoules, which are provided with means to prevent accidental engagement between the hypodermic needle and the cartridge ampoule and consequent premature discharge of the ampoule contents prior to intended use of the syringes.

(b) Description of the Prior Art

It is known in prepackaged hypodermic syringes, for example as illustrated by Keller U.S. Pat. No. 3,375,825, to use a hypodermic needle sheath to serve a second function as a plunger rod. It is also known, for example as described by Maki U.S. Pat. No. 3,150,661, to use an annular projection or ridge around the inside perimeter of a hypodermic needle hub unit to lock into a mating annular groove around the outside perimeter of a crimped-on metal overcap of a cartridge ampoule in order to maintain the inner end of a double ended hypodermic needle affixed to the needle hub out of piercing engagement with the diaphragm closing the inner end of the cartridge ampoule.

However, it is not believed known in the prior art to employ the concept involved in the present invention for preventing accidental piercing of the cartridge ampoule diaphragm by the inner end of a double-ended hypodermic syringe needle comprising either (a) reversing the cartridge ampoule within the barrel of the syringe holder and further providing the latter with means for restraining movement of the ampoule within the syringe barrel or (b) providing such restraint means within the syringe barrel with the cartridge ampoule is properly oriented within the syringe barrel for use.

BRIEF SUMMARY OF THE INVENTION

As will be seen, certain of the embodiments of the present invention employ reversible elements of the various hypodermic syringes which are contemplated. Therefore in order to avoid confusion, in the discussion throughout the specification as well as in the appended claims, the terms "lower" and "downward" are intended to refer to the needle end of the syringes and their associated parts as assembled for injection use, and conversely the terms "upper", "inner" and "upward" refer to the head end of the same as assembled for injecting use.

In one of its embodiments, the invention relates to a prepackaged, disposable hypodermic syringe comprising a syringe holder having a barrel, an end closure cap removably affixed to the upper end of the barrel, the lower end being provided with an integral double-ended needle and needle hub, a combination needle sheath and plunger frictionally engaged with the needle hub and covering the needle when the syringe is not in use and a cartridge ampoule containing an injectable fluid therein and which is sealed at its upper end by a slidable piston and at its lower end by a pierceable diaphragm. When not in use, such as when being stored or when being shipped in commerce, the cartridge ampoule is carried within the barrel of the syringe in reverse orientation with respect to the hypodermic needle, and engagement of the inner end of the hypodermic needle with the slidable piston of the cartridge ampoule is prevented by restraint means in the lower end of the syringe barrel. The invention also relates to the syringe holder per se of the above described first embodiment of a prepackaged, disposable hypodermic syringe.

In a second embodiment, the invention relates to a prepackaged, disposable hypodermic syringe comprising a syringe holder having a barrel, an end closure cap removably affixed to one end of the barrel, the other end being provided with a detachable double-ended hypodermic needle and needle hub, a combination needle sheath and plunger frictionally engaged with the needle hub and covering the needle when the syringe is not in use and a cartridge ampoule containing an injectable fluid therein and which is sealed at its upper end by a slidable piston and at its lower end by a pierceable diaphragm. When not in use, the detachable needle and needle hub unit with the frictionally engaged needle sheath/plunger attached thereto is attached to, and serves to close, the upper end of the syringe barrel, and the closure cap is removably affixed to the lower end thereof. Engagement of the upper end of the cartridge ampoule with the inner end of the hypodermic needle when the parts are assembled in the storage configuration is prevented by restraint means in the upper end of the syringe barrel. The invention also relates to the syringe holder per se of the above-described second embodiment of a prepackaged, disposable hypodermic syringe.

In a third embodiment, the invention relates to a prepackaged, disposable hypodermic syringe comprising a syringe holder having a barrel, the barrel being provided at its lower end with an integral double-ended needle and needle hub, a combination needle sheath and plunger frictionally engaged with the needle hub and covering the needle when the syringe is not in use and a cartridge ampoule containing an injectable fluid therein and which is sealed at its upper end by a slidable piston and at its lower end by a pierceable diaphragm. The syringe is fitted on the side of the barrel with a detachable safety plate having locking tabs which serve to prevent engagement of the inner end of the hypodermic needle with the pierceable diaphragm of the cartridge ampoule. The invention also relates to the syringe holder per se of the above-described third embodiment of a prepackaged, disposable hypodermic syringe.

BRIEF DESCRIPTION OF THE DRAWINGS

FIGS. 1A, 1B and 1C are longitudinal section views depicting one embodiment of the prepackaged hypodermic syringes of the invention showing the elements thereof as assembled for shipment or storage; as partially reassembled prior to use; and as fully reassembled for use with the cartridge ampoule contents partially discharged, respectively.

FIGS. 2A, 2B and 2C are longitudinal section views depicting a second embodiment of the prepackaged hypodermic syringes of the invention showing the elements thereof as assembled for shipment or storage; as partially reassembled prior to use; and as fully reassembled for use with the cartridge ampoule contents partially discharged, respectively.

FIG. 3A is an elevational view of a third embodiment of the prepackaged hypodermic syringes of the invention showing the exteriorly visible elements thereof as assembled for shipment or storage.

FIGS. 3B, 3C and 3D are longitudinal section views of the embodiment of the prepackaged hypodermic syringe depicted in FIG. 3A, FIG. 3B being a view in section on line 3B—3B of FIG. 3A, and showing the elements thereof as assembled for shipment or storage; as being readied for use by removal of a safety plate to be described further hereinbelow; and with all elements fully oriented for use with the cartridge ampoule contents partially discharged, respectively.

DETAILED DESCRIPTION OF THE INVENTION

The invention will now be described in detail with reference to the foregoing figures where like numerals are used to designate like parts.

Figure 5:
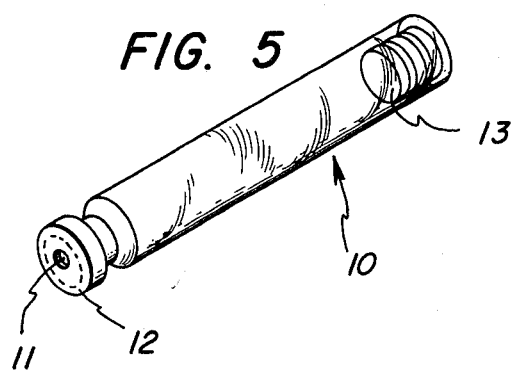
FIG. 5 is a perspective view of a cartridge ampoule used with the prepackaged hypodermic syringes of the invention.

FIG. 5 illustrates a cartridge ampoule, generally indicated by reference numeral 10, of a well-known type which consists of a cylindrical container, usually glass or clear plastic, having a necked-down end and sealed at the necked-down end with a diaphragm 11 which is secured to the ampoule by a crimped on metal collar 12. The other end of the ampoule is closed by a piston 13 which is slidable within the bore of the ampoule.

The cartridge ampoules, such as depicted in FIG. 5, are used in combination with the prepackaged, disposable syringes of the present invention, one embodiment of which is depicted in FIGS. 1A, 1B and 1C. FIG. 1A depicts the combination of a cartridge ampoule within a disposable syringe holder as the prepackaged unit would be assembled for shipment or storage prior to use. In this embodiment, the cartridge ampoule 10 is carried within the barrel of a syringe holder represented by the general reference numeral 14. The syringe holder comprises a barrel 15 having a double-ended hypodermic needle 16 within an integral needle hub unit 17. The end of the needle extending outside the needle hub is protected by a needle sheath 18 having an enlarged annular collar 19 which is frictionally engaged with the needle hub 17. The upper end of the barrel is closed by a removable closure cap 20. The closure cap has a hole 21 of sufficient bore to slidably receive the outside diameter of the needle sheath 18 for a purpose to be described hereinbelow. When the syringe holder and cartridge ampoule combination is either being shipped or held in storage prior to use, the ampoule 10 is carried within the barrel 15 in reversed, or head-for-tail, orientation, that is, with the piston end of the cartridge ampoule adjacent the inner end of the double-ended needle. The lower end of barrel 15 is provided with a shoulder 22 which engages the rim 31 of the piston end of the cartridge ampoule. The relative position of the shoulder 22 with respect to the inner end of the needle should be such as to preclude communication of the needle through the piston 13 with the contents of the cartridge ampoule when the rim 31 of cartridge ampoule 10 is in engagement with shoulder 22. Preferably, contact of the needle with the piston is avoided completely as depicted in FIG. 1A.

When it is desired to use the syringe, the end closure cap 20 is removed, the cartridge ampoule 10 is removed from the barrel, turned end-for-end and reinserted in the barrel 15, and the closure cap is reattached. The reorientation of the parts is shown in FIG. 1B. Thereafter, the needle sheath 18 is detached from the needle hub 17, and the lower end of the sheath is inserted through the hole 21 in the closure cap 20. Downward pressure upon the collar 19 forces the ampoule downward until the lower end thereof, that is the necked-down end which is sized such that it by-passes shoulder 22, enters and seats within cavity 23, with concomitant piercing of diaphragm 11 by the inner end of needle 16. When repositioned as described above, the needle sheath thus serves a second function as a plunger, and the enlarged collar 19 serves as a thumb plate. The ampoule contents can thus be expelled upon further downward motion of the plunger as shown by the arrow in FIG. 1C.

A second embodiment of prepackaged disposable hypodermic syringes contemplated by the present invention is depicted in FIGS. 2A, 2B and 2C. The prepackaged cartridge ampoule and syringe holder combination as assembled for shipment or storage is depicted in FIG. 2A. In this embodiment, as in that of the embodiment of FIGS. 1A, 1B and 1C, the cartridge ampoule 10 is carried within the barrel 15 of the syringe holder in reverse orientation relative to the hypodermic needle. Contact between the slidable piston 13 and the inner end of the hypodermic needle is prevented by abutment of the rim 31 of the cartridge ampoule against an annular rim 24. This embodiment is fitted with a removable closure cap 20 closing one end of the barrel 15, the other end thereof being closed by a removable plug 25 integral with the needle hub/needle section and having a cavity 23' in the inner end of the plug. When it is desired to use the syringe depicted in FIG. 2A, the closure cap 20 and the removable plug 25 are detached from their respective ends of the barrel 15 and interchanged one with the other, the closure cap being attached to the end formerly used to attach the plug, and the plug being attached to the end formerly used to attach the closure cap. When so repositioned, the elements of the combination have the relative positions with respect to one another shown in FIG. 2B, the interchange of the closure cap 20 and plug 25 in effect bringing about a reversal of the cartridge ampoule 10 relative to the hypodermic needle 16. Thereafter, relocation of the needle sheath through the hole 21 in closure cap 20 and downward pressure against the annular collar/thumb plate 19 forces the diaphragm end of the cartridge ampoule down into cavity 23' with resultant piercing of the diaphragm by the inner end of the hypodermic needle 16 as shown in FIG. 2C. Further downward pressure on the thumb plate as indicated by the arrow in FIG. 2C causes expulsion of the ampoule contents.

A further embodiment of the invention is shown in FIGS. 3A, 3B, 3C and 3D. This embodiment, as prepackaged for shipment and storage, is shown in elevation in FIG. 3A and in longitudinal section in FIG. 3B. In this embodiment, the cartridge ampoule 10 is carried within the barrel 15 of the syringe holder 14 with the diaphragm end oriented towards the double-ended hypodermic needle. The barrel is closed at its upper end by removable closure cap 20 having a hole 21 therethrough and is equipped at its lower end with a needle sheath/plunger 18 frictionally engaged with the needle hub structure 17. In the prepackaged assembly of the components, the syringe is provided with a removable safety plate 26 which is provided at its lower end with a locking tab 27 joined to the plate generally normal to the plane thereof. The locking tab passes through a slot 28 in the side wall of the barrel and supports the lower end of the cartridge ampoule 10 against downward movement so as to prevent piercing of the diaphragm 11 by the inner end of the needle 16. The upper end of safety plate 26 is fitted with a second locking tab 27' which passes through a slot 28' in the side wall adjacent the upper end of the syringe barrel. The distances between the tabs 27 and 27' and the slots 28 and 28' is chosen so as to provide a secure frictional fit of the tabs in the slots in order that the safety plate will not be accidentally disengaged.

When it is desired to use the syringe depicted in FIGS. 3A and 3B, the tab 27' at the upper end of the safety plate is disengaged from its corresponding slot 28' by prying outward, for example with a finger nail, as depicted in FIG. 3C. The safety plate can then be entirely removed from the syringe barrel and, as depicted in FIG. 3D and as previously described above in connection with FIGS. 1C and 2C, the needle sheath can be detached from the needle hub, inserted through the hole 21 in closure cap 20 and used as a plunger to effect, first, seating of the ampoule against the lower end of the barrel and piercing of the diaphragm 11 by the inner end of needle 16 and, then, expulsion of the ampoule contents as depicted in FIG. 3D.

It will be understood that, although the preferred embodiments have been described above in order to better illustrate the invention, alternative structural features can be substituted for elements specifically described herein without either departing from the spirit of the invention or in any way adversely affecting the operability of the same.

Figure 4:
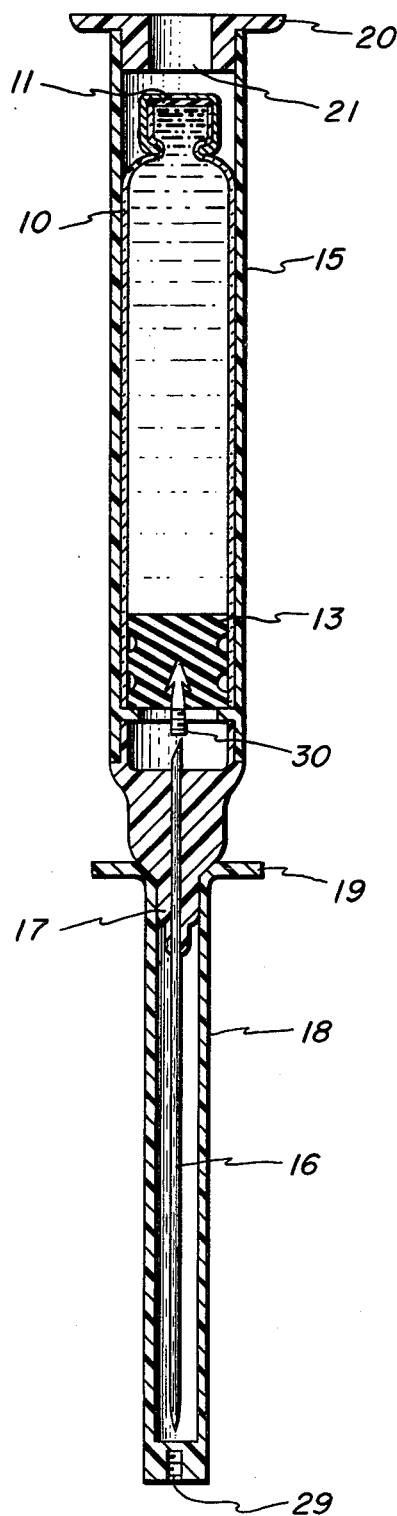
FIG. 4 is a longitudinal section view showing an alternative prepackaged hypodermic syringe of the type shown in FIGS. 2A, 2B and 2C and adapted to permit manual aspiration.

For example, the prepackaged hypodermic syringes of the invention have been described above in terms of the use of a plunger rod 18 which is not inter-engaged with the slidable piston 13. The syringes as thus configured cannot function as aspirating syringes. However, it will be appreciated by those skilled in the art that all the syringes of the invention here-described can be adapted for manual aspirating capability by merely providing a means for inter-engaging the plunger 18 with the piston 13. One means of achieving such inter-engagement with one of the embodiments described herein is depicted in FIG. 4 which shows a modification of the embodiment shown in FIGS. 2A, 2B and 2C. In the embodiment of FIG. 4, the tip of the needle sheath/plunger 18 is provided with a threaded hole 28 which mates with a threaded post 30 molded into the slidable piston 13. While this means of achieving inter-engagement has been shown here for purposes of illustration, it is to be understood that all of the embodiments of the invention here-described can be adapted for aspirating capability by the inclusion of any conventional means of achieving the necessary plunger/piston inter-engagement well-known in the prior art.

Moreover, although the embodiments represented by FIGS. 2A, 2B, 2C and 4 have been described in terms of a continuous annular rim 24 which serves as the restraint means for preventing contact between the ampoule piston and the inner end of the hypodermic needle, obviously any alternative structure, such as a series of tabs, or even a single tab, which will serve the same purpose would be fully operative, and such alternative structures are considered to be within the purview of the invention.

The prepackaged hypodermic syringes, that is the syringe holders and their associated cartridge ampoules, as well as the syringe holders themselves, are intended as single use, disposable units. The cartridge ampoules, a indicated above, are well known in the art and are generally constructed of glass, the piston and pierceable diaphragm being of a flexible material, such as natural or synthetic rubber or flexible plastic. The syringe holders are preferably made of plastic, such as polystyrene, polyethylene, polypropylene, polyvinyl chloride or the like.

Having thus described the invention and the advantages thereof, it is considered that the invention is to be broadly construed and limited only by the character of the following claims.

I claim:

1. A hypodermic syringe package for use in combination with a cartridge ampoule, said ampoule being sealed at its upper end by a slidable piston and at its lower end by a pierceable diaphragm and containing an injectable fluid therein, said package being adapted to prevent communication between an associated hypodermic syringe needle and the contents of said ampoule when said package is in a storage or pre-use configuration, which package comprises:

a syringe holder having a barrel; an end closure cap removably attached to one end of said barrel, and a double-ended needle and needle hub removably attached to the other end of said barrel; and restraint means within said barrel adjacent the needle/needle hub end thereof when in said storage configuration, said restraint means comprising either an annular rim, a single tab or multiple tabs on the inside of said barrel adjacent the upper end thereof, said restraint means serving to prevent communication between the inner end of said double-ended needle and the contents of a cartridge ampoule when held within said barrel and whereby, upon interchange of said end closure cap and said needle and needle hub on the ends of said barrel to thereby assemble said syringe and cartridge ampoule into a use configuration, said restraint means no longer prevents communication between the inner end of said double-ended needle and the ampoule contents.

2. A hypodermic syringe package according to claim 1 wherein said needle and needle hub are integral with a removable plug attached to said syringe barrel.

3. A hypodermic syringe package according to claim 2 which includes a needle sheath frictionally attached to said needle hub.

4. A hypodermic syringe package according to claim 1 which includes a needle sheath frictionally attached to said needle hub.

5. A hypodermic syringe package according to claim 3 wherein said closure cap has an axial hole therethrough for slidably receiving said needle sheath for use thereof as a plunger.

6. A hypodermic syringe package according to claim 4 wherein said closure cap has an axial hole therethrough for slidably receiving said needle sheath for use thereof as a plunger.

7. A hypodermic syringe package according to claim 5 wherein said needle sheath is provided with an annular collar for use as a thumb plate.

8. A hypodermic syringe package according to claim 6 wherein said needle sheath is provided with an annular collar for use as a thumb plate.

9. A hypodermic syringe package according to claim 8 wherein said safety plate has a pair of locking tabs and wherein said locking tabs are inserted through slots in the side wall of said barrel.

10. A hypodermic syringe package according to claim 7 wherein said needle sheath is provided with means for making positive engagement with the slidable piston in the upper end of a cartridge ampoule.

11. A hypodermic syringe package according to claim 9 wherein said needle sheath is provided with means for making positive engagement with the slidable piston in the upper end of a cartridge ampoule.

12. A hypodermic syringe package according to claim 10 wherein said positive engagement means comprises a threaded hole in the tip of said needle sheath in combination with a mating threaded post on said slidable piston.

13. A hypodermic syringe package according to claim 11 wherein said positive engagement means comprises a threaded hole in the tip of said needle sheath in combination with a mating threaded post on said slidable piston.

14. A hypodermic syringe package for use in combination with a cartridge ampoule, said ampoule being sealed at its upper end by a slidable piston and at its lower end by a pierceable diaphragm and containing an injectable fluid therein, said package being adapted to prevent communication between an associated hypodermic syringe needle and the contents of said ampoule; when said package is in a storage or pre-use configuration, which package comprises:
a syringe holder having a barrel; an end closure cap removably attached to one end of said barrel, and a double-ended needle and needle hub removably attached to the other end of said barrel; and restraint means within said said barrel adjacent the needle/needle hub end thereof when in said storage configuration, said restraint means comprising a removable safety plate having a locking tab affixed thereto and positioned within the lower end of said barrel
said restraint means serving to prevent communication between the inner end of said double-ended needle and the contents of a cartridge ampoule when held within said barrel and whereby, upon removal of said safety plate, said restraint means no longer prevents communication between the inner end of said double-ended needle and the ampoule contents.

15. A hypodermic syringe package according to claim 14 wherein said needle and needle hub are integral with said syringe barrel.

16. A prepackaged hypodermic syringe which, in a storage or pre-use configuration, comprises in combination:
(A) a syringe holder having a barrel; an end closure cap removably attached to one end of said barrel, and a double-ended needle and needle hub removably attached to the other end of said barrel; and restraint means within said barrel adjacent the needle/needle hub end thereof, said restraint means comprising either an annular rim, a single tab or multiple tabs in the inside of said barrel adjacent the upper end thereof; and
(B) a cartridge ampoule within said barrel, said cartridge ampoule being sealed at its upper end by a slidable piston and at its lower end by a pierceable diaphragm and containing an injectable fluid therein,
whereby said restraint means prevents communication between the inner end of said double-ended needle and the contents of said cartridge ampoule when held within said barrel in a pre-use configuration and whereby, upon interchange of said end closure cap and said needle and needle hub on the ends of said barrel to thereby assemble said syringe and cartridge ampoule into a use configuration, said restraint means no longer prevents communication between the inner end of said double-ended needle and said ampoule contents.

17. A prepackaged hypodermic syringe according to claim 16 wherein said needle and needle hub are integral with a removable plug attached to said syringe barrel.

18. A prepackaged hypodermic syringe according to claim 17 which includes a needle sheath frictionally attached to said needle hub.

19. A prepackaged hypodermic syringe according to claim 1 which includes a needle sheath frictionally attached to said needle hub.

20. A prepackaged hypodermic syringe according to claim 18 wherein said closure cap has an axial hole therethrough for slidably receiving said needle sheath for use thereof as a plunger.

21. A prepackaged hypodermic syringe according to claim 19 wherein said closure cap has an axial hole therethrough for slidably receiving said needle sheath for use thereof as a plunger.

22. A prepackaged hypodermic syringe according to claim 20 wherein said needle sheath is provided with an annular collar for use as a thumb plate.

23. A prepackaged hypodermic syringe according to claim 21 wherein said needle sheath is provided with an annular collar for use as a thumb plate.

24. A prepackaged hypodermic syringe according to claim 23 wherein said safety plate has a pair of locking tabs and wherein said locking tabs are inserted through slots in the side wall of said barrel.

25. A prepackaged hypodermic syringe according to claim 22 wherein said needle sheath and said cartridge ampoule are provided with means for making positive engagement with the slidable piston in the upper end of said cartridge ampoule.

26. A prepackaged hypodermic syringe according to claim 24 wherein said needle sheath and said cartridge ampoule are provided with means for making positive engagement with the slidable piston in the upper end of said cartridge ampoule.

27. A prepackaged hypodermic syringe according to claim 25 wherein said positive engagement means comprises a threaded hole in the tip of said needle sheath in combination with a mating threaded post on said slidable piston.

28. A prepackaged hypodermic syringe according to claim 26 wherein said positive engagement means comprises a threaded hole in the tip of said needle sheath in combination with a mating threaded post on said slidable piston.

29. A prepackaged hypodermic syringe which, in a storage or pre-use configuration, comprises in combination:
(A) a syringe holder having a barrel; an end closure cap removably attached to one end of said barrel and a double-ended needle and needle hub removably attached to the other end of said barrel; and restraint means within said barrel adjacent the needle/needle hub end thereof, said restraint means comprising a removable safety plate having a locking tab affixed thereto and positioned within the lower end of said barrel; and
(B) a cartridge ampoule within said barrel, said cartridge ampoule being sealed at its upper end by a slidable piston and at its lower end by a pierceable diaphragm and containing an injectable fluid therein,
whereby said restraint means prevents communication between the inner end of said double-ended needle and the contents of said cartridge ampoule when held within said barrel in a pre-use configuration and whereby, upon removal of said safety plate, said restraint means no longer prevents communication between the inner end of said double-ended needle and the ampoule contents.

30. A prepackaged hypodermic syringe according to claim 29 wherein said needle and needle hub are integral with said syringe barrel.

* * * * *

UNITED STATES PATENT AND TRADEMARK OFFICE
CERTIFICATE OF CORRECTION

PATENT NO.   :   4,445,895
DATED        :   May 1, 1984
INVENTOR(S)  :   H. Margulies It is certified that error appears in the above-identified patent and that said Letters Patent are hereby corrected as shown below:

Column 1, line 7, change "filed July 16, 1981" to read
-- ...filed July 16, 1981, now abandoned. --

Column 5, line 14, change "is chosen" to read
-- are chosen --.

Column 5, line 53, change "hole 28" to read
-- hole 29 --.

Column 6, line 8, change "a indicated" to read
-- as indicated --.

Signed and Sealed this

Twenty-third Day of April 1985

[SEAL]

Attest:

DONALD J. QUIGG

Attesting Officer       Acting Commissioner of Patents and Trademarks